US007081450B2

(12) United States Patent
Goldshtein

(10) Patent No.: US 7,081,450 B2
(45) Date of Patent: *Jul. 25, 2006

(54) WATER SOLUBLE NANOPARTICLES OF HYDROPHILIC AND HYDROPHOBIC ACTIVE MATERIALS AND AN APPARATUS AND METHOD FOR THEIR PRODUCTION

(75) Inventor: Rina Goldshtein, Har Hebron (IL)

(73) Assignee: Solubest Ltd., Ness Ziona (IL)

( * ) Notice: Subject to any disclaimer, the term of this patent is extended or adjusted under 35 U.S.C. 154(b) by 48 days.

This patent is subject to a terminal disclaimer.

(21) Appl. No.: 10/256,023

(22) Filed: Sep. 26, 2002

(65) Prior Publication Data

US 2003/0129239 A1 Jul. 10, 2003

Related U.S. Application Data

(63) Continuation-in-part of application No. 09/966,847, filed on Sep. 28, 2001, now Pat. No. 6,878,693.

(51) Int. Cl.
*A01N 43/04* (2006.01)
*A61K 31/715* (2006.01)

(52) U.S. Cl. ............................ 514/54; 514/42; 514/43; 514/57; 424/489; 424/499; 424/500; 424/501; 536/22.1; 536/123; 536/124

(58) Field of Classification Search .................. 514/42, 514/43, 54, 57; 424/489, 499, 500, 501; 536/22.1, 123, 124
See application file for complete search history.

(56) References Cited

U.S. PATENT DOCUMENTS

| | | | | |
|---|---|---|---|---|
| 5,145,684 | A * | 9/1992 | Liversidge et al. | 424/489 |
| 5,589,194 | A | 12/1996 | Tsuei et al. | 424/497 |
| 5,629,021 | A | 5/1997 | Wright | 424/489 |
| 5,693,608 | A | 12/1997 | Bechgaard et al. | 514/2 |
| 5,734,071 | A | 3/1998 | Fex et al. | 554/186 |
| 5,760,015 | A | 6/1998 | Joulliè et al. | 514/58 |
| 5,766,635 | A | 6/1998 | Spenleuhauer et al. | 424/489 |
| 5,817,332 | A | 10/1998 | Urtti et al. | 424/449 |
| 5,854,226 | A | 12/1998 | Penkler et al. | 514/58 |
| 6,010,718 | A * | 1/2000 | Al-Razzak et al. | 424/464 |
| 6,015,574 | A | 1/2000 | Cannell et al. | 424/450 |
| 6,120,794 | A | 9/2000 | Liu et al. | 424/450 |
| 6,143,321 | A | 11/2000 | Needham et al. | 424/450 |
| 6,197,757 | B1 | 3/2001 | Perrier et al. | 514/53 |
| 6,207,180 | B1 | 3/2001 | Ottoboni et al. | 424/426 |
| 6,217,886 | B1 | 4/2001 | Önyüksel et al. | 424/401 |
| 6,221,389 | B1 | 4/2001 | Cannell et al. | 424/450 |
| 6,221,399 | B1 * | 4/2001 | Rolfes et al. | 424/489 |
| 6,224,794 | B1 | 5/2001 | Amsden et al. | 264/4.1 |
| 6,225,063 | B1 | 5/2001 | Khvorova et al. | 435/6 |
| 6,228,399 | B1 * | 5/2001 | Parikh et al. | 424/489 |
| 6,656,504 | B1 * | 12/2003 | Bosch et al. | 424/489 |

FOREIGN PATENT DOCUMENTS

| | | |
|---|---|---|
| EP | 1 127 570 A2 | 8/2001 |
| WO | WO 97/04756 | 2/1997 |
| WO | WO 97/10849 | 3/1997 |
| WO | WO 00/74658 A1 | 12/2000 |

OTHER PUBLICATIONS

Akiyoshi, et al., "Hydrogel Nanoparticle Formed by Self-Assembly of Hydrophobized Polysaccharide. Stabilization of Adriamycin by Complexation", *Eur. J. Pharm. Biopharm.*, 42(4):286-290 (1996).

Allémann, et al., "Drug-Loaded Nanoparticles—Preparation Methods and Drug Targeting Issues", *Eur. J. Pharm. Biopharm.*, 39(5):173-191 (1993).

Chung, et al., "Thermo-Responsive Drug Delivery from Polymeric Micelles Constructed Using Block Copolymers of Poly(N-Isopropylacrylamide) and Poly(Butylmethacrylate", *J. Controlled Release*, 62(1-2):115-127 (1999).

Database WPI, Section Ch, Week 200041, Abstract, Derwent Publications Ltd., London, GB, AN 1993-290554, XP-002248301 & Jp. 03 072340 B (Pola Chem. Ind. Inc.) Jul. 2000.

Invitation to Pay Additional Fees (Form PCT/ISA/206) for PCT/IB02/04176 mailed Nov. 4, 3003.

Jones, et al., "Polymeric Micelles—A New Generation of Colloidal Drug Carriers", *Eur. J. Pharm. Biopharm.*, 48(2):101-111 (1999).

Jung, et al., "Sulfobutylated Poly(Vinyl Alcohol)-Graft-Poly(Lactide-co-Glycolide)s Facilitate the Preparation of Small Negatively Charged Biodegradable Nanospheres", *J. Controlled Release*, 67(2-3):157-169 (2000).

Kwon, et al., "Block Copolymer Micelles for Drug Delivery: Loading and Release of Doxorubicin", *Journal of Controlled Release*, 48(2-3):195-201 (1997).

Labhasetwar, et al., "Nanoparticles—A Colloidal Drug Delivery System for Primaquine and Metronidazole", *J. Controlled Release*, 12(2):113-119 (1990).

Pavanetoo, et al., "Evaluation of Process Parameters Involved in Chitosan Microsphere Preparation by the o/w/o Multiple Emulsion", *J. Microencapsulation*, 13(6):679-688 (1996).

(Continued)

*Primary Examiner*—Patrick Lewis
(74) *Attorney, Agent, or Firm*—Browdy and Neimark, PLLC

(57) ABSTRACT

This invention provides a soluble nano-sized particles formed of a core (water-insoluble lipophilic compound or hydrophilic compound) and an amphiphilic polymer and which demonstrated improved solubility and/or stability. The lipophilic compound within the soluble nano-sized soluble ("solu-nanoparticles") may consist of pharmaceutical compounds, food additives, cosmetics, agricultural products and veterinary products. The invention also provides novel methods for preparing the nano-sized soluble particles, as well as a novel chemical reactor for manufacturing an inclusion complex comprising the nano-sized soluble particles.

28 Claims, 8 Drawing Sheets

OTHER PUBLICATIONS

Rolland, et al., "New Macromolecular Carriers for Drugs. I. Preparation and Characterization of Poly(Oxiethylene-b-Isoprene-b-Oxyethylene) Block Copolymer Aggregates", *J. Applied Polymer Sci*., 44(7):1195-1203 (1992).

Zhang, et al., "Increase in Gentamicin Uptake by Cultured Mouse Peritoneal Macrophages and Rat Hepatocytes by its Binding to Polybutylcyanoacrylate Manoparticles", *Intl. J. Pharm*., 164(1-2):21-27 (1998).

* cited by examiner

PHARMACOKINETICS (PK)-CONSTANTS OF TESTED COMPLEXED CLARITHROMYCIN IN COMPARISON TO PUBLISHED DATA OF COMMERCIAL DRUG

| | | COMPLEXED CLARITHROMYCIN | COMMERCIAL CLARITHROMYCIN |
|---|---|---|---|
| Dosing_time | Hr | 0.0000 | 0.0000 |
| Rsq | | 0.9973 | 0.9690 |
| Rsq(adjusted) | | 0.9960 | 0.9534 |
| Corr(x:y) | | -0.9987 | -0.9844 |
| Tlag | Hr | 0.0000 | 0.0000 |
| Tmax | Hr | 4.0000 | 1.0000 |
| Cmax | Ng/mL | 5116.0000 | 4000.0000 |
| No._points_Lambda_z | | 4.0000 | 4.0000 |
| Tlast | Hr | 24.0000 | 6.0000 |
| Clast | Ng/mL | 17.0000 | 700.0000 |
| AUClast | Hr*ng/mL | 54193.5000 | 10100.0000 |
| Lambda_z | 1/hr | 0.3056 | 0.3008 |
| Lambda_z_lower | Hr | 4.0000 | 1.0000 |
| Lambda_z_upper | Hr | 24.0000 | 6.0000 |
| t1/2_Lambda_z | Hr | 2.2683 | 2.3040 |
| AUCall | Hr*ng/mL | 54193.5000 | 10100.0000 |
| AUCINF(observed) | Hr*ng/mL | 54249.1320 | 12426.7693 |
| AUCINF(observed)/D | Hr*ng/mL/mg*kg | 216.9965 | 62.1338 |
| AUC_%Extrap(obs.) | % | 0.1025 | 18.7238 |
| Vz(observed)/F | mL/kg | 15080.7530 | 53496.7066 |
| Cl(observed)/F | mL/hr/kg | 4608.3687 | 16094.2877 |
| AUCINF(predicted) | Hr*ng/mL | 54249.1503 | 12373.8114 |
| AUCINF(predicted)/D | Hr*ng/mL/mg*kg | 216.9966 | 61.8691 |
| AUC_%Extrap(pred.) | % | 0.1026 | 18.3760 |
| Vz(predicted)/F | mL/kg | 15080.7479 | 53725.6639 |
| Cl(predicted)/F | mL/hr/kg | 4608.3671 | 16163.1686 |
| AUMClast | Hr*hr*ng/mL | 325307.0000 | 23800.0000 |
| AUMCINF(observed) | Hr*hr*ng/mL | 326824.2223 | 45494.6951 |
| AUMC_%Extrap(obs.) | % | 0.4642 | 47.6862 |
| AUMCINF(predicted) | Hr*hr*ng/mL | 326824.7202 | 45000.9178 |
| AUMC_%Extrap(pred.) | % | 0.4644 | 47.1122 |
| MRTlast | Hr | 6.0027 | 2.3564 |
| MRTINF(observed) | Hr | 6.0245 | 3.6610 |
| MRTINF(predicted) | Hr | 6.0245 | 3.6368 |

Fig. 3

WATER SOLUBLE NANOPARTICLES OF HYDROPHILIC AND HYDROPHOBIC ACTIVE MATERIALS AND AN APPARATUS AND METHOD FOR THEIR PRODUCTION

FIELD OF THE INVENTION

The invention is in the field of nanoparticles. More particularly, the invention relates to soluble nano-sized particles ("solu-nanoparticles") and methods of producing solu-nanoparticles that render insoluble compounds solubilized in a medium otherwise not soluble.

BACKGROUND OF THE INVENTION

Two formidable barriers to effective drug delivery and hence to disease treatment, are solubility and stability. To be absorbed in the human body, a compound has to be soluble in both water and fats (lipids). Solubility in water is, however, often associated with poor fat solubility and vice versa.

Over one third of drugs listed in the U.S. Pharmacopoeia and about 50% of new chemical entities (NCEs) are insoluble or poorly insoluble in water. Over 40% of drug molecules and drug compounds are insoluble in the human body. In spite of this, lipophilic drug substances having low water solubility are a growing drug class having increasing applicability in a variety of therapeutic areas and for a variety of pathologies. There are over 2500 large molecules in various stages of development today, and over 5500 small molecules in development (See Drug Delivery Companies Report 2001, p. 2, www.pharmaventures.com). Each of the existing companies focusing on these large and small molecules has its own restriction and limitations with regard to both large and small molecules on which they focus.

Solubility and stability issues are major formulation obstacles hindering the development of therapeutic agents. Aqueous solubility is a necessary but frequently elusive property for formulations of the complex organic structures found in pharmaceuticals. Traditional formulation systems for very insoluble drugs have involved a combination of organic solvents, surfactants and extreme pH conditions. These formulations are often irritating to the patient and may cause adverse reactions. At times, these methods are inadequate for solubilizing enough of a quantity of a drug for a parenteral formulation. In such cases, doctors may administer an "overdosage", such as for example with poorly soluble vitamins. In most cases, this overdosage does not cause any harm since the unabsorbed quantities exit the body with urine. Overdosage does, however waste a large amount of the active compound.

The size of the drug molecules also plays a major role in their solubility and stability as well as bioavailability. Bioavailability refers to the degree to which a drug becomes available to the target tissue or any alternative in vivo target (i.e., receptors, tumors, etc.) after being administered to the body. Poor bioavailability is a significant problem encountered in the development of pharmaceutical compositions, particularly those containing an active ingredient that is poorly soluble in water. Poorly water soluble drugs tend to be eliminated from the gastrointestinal tract before being absorbed into the circulation. It is known that the rate of dissolution of a particulate drug can increase with increasing surface area, that is, decreasing particle size Recently, there has been an explosion of interest in nanotechnology, the manipulation on the nanoscale. Nanotechnology is not an entirely new field; colloidal sols and supported platinum catalysts are nanoparticles. Nevertheless, the recent interest in the nanoscale has produced, among numerous other things, materials used for and in drug delivery. Nanoparticles are generally considered to be solids whose diameter is varies between 1–1000 nm.

Although a number of solubilization technologies do exist, such as liposomes, cylcodextrins, microencapuslation, and dendrimers, each of these technologies has a number of significant disadvantages.

Phospholipids exposed to aqueous environment form a bi-layer structure called liposomes. Liposomes are microscopic spherical structures composed of phospholipids that were first discovered in the early 1960s (Bangham et al., J. Mol. Biol. 13: 238 (1965)). In aqueous media, phospholipid molecules, being amphiphilic, spontaneously organize themselves in self-closed bilayers as a result of hydrophilic and hydrophobic interactions. The resulting vesicles, referred to as liposomes, therefore encapsulate in the interior part of the aqueous medium in which they are suspended, a property that makes them potential carriers for biologically active hydrophilic molecules and drugs in vivo. Lipophilic agents may also be transported, embedded in the liposomal membrane. Liposomes resemble the bio-membranes and have been used for many years as a tool for solubilization of biological active molecules insoluble in water. They are non-toxic and biodegradable and can be used for specific target organs.

Liposome technology allows for the preparation of smaller to larger vesicles, using unilamillar (ULV) and multilamillar (MLV) vesicles. MLV are produced by mechanical agitation. Large ULV are prepared from MLV by extrusion under pressure through membranes of known pore size. The sizes are usually 200 nm or less in diameter, however, liposomes can be custom designed for almost any need by varying lipid content, surface change and method of preparation.

A number of companies such as Elan, Corp., Dublin, Ireland; Endorex Corp., Lake Forest, Ill.; Advanced Drug Deliveries Technologies, Muttenz, Switzerland; The Liposome Company, Inc., Princeton, N.J. (a subsidiary of Elan, Corp.); and Mibelle AG, Buchs, Switzerland, offer contract research and production facilities to the industry for the preparation of liposome inclusion complexes or inclusion moieties.

As drug carriers, liposomes have several potential advantages, including the ability to carry a significant amount of drug, relative ease of preparation, and low toxicity if natural lipids are used. However, common problems encountered with liposomes include: low stability, short shelf-life, poor tissue specificity, and toxicity with non-native lipids. Additionally, the uptake by phagocytic cells reduces circulation times. Furthermore, preparing liposome formulations that exhibit narrow size distribution has been formidable challenge under demanding conditions, as well as a costly one. Also, membrane clogging often results during the production of larger volumes required for pharmaceutical production of a particular drug.

Cyclodextrins are crystalline, water soluble, cyclic, non-reducing oligosaccharides built from six, seven, or eight glucopyranose units, referred to as alpha, beta and gamma cyclodextrin respectively, which have long been known as products that are capable of forming inclusion complexes. The cyclodextrin structure provides a molecule shaped like a segment of a hollow cone with an exterior hydrophilic surface and interior hydrophobic cavity.

The hydrophilic surface generates good water solubility for the cyclodextrin and the hydrophobic cavity provides a favorable environment in which to enclose, envelope or entrap the drug molecule. This association isolates the drug from the aqueous solvent and may increase the drug's water solubility and stability. For a long time most cyclodextrins had been no more than scientific curiosities due to their limited availability and high price.

As a result of intensive research and advances in enzyme technology, cyclodextrins and their chemically modified derivatives are now available commercially, generating a new technology: packing on the molecular level. Companies such as Cyclolab Ltd., Budapest, Hungary; Cydex, Inc., Overland Park, Kans.; and Cyclops, Inc., Reykjavik, Iceland, have been involved in the development and manufacture of cyclodextrins.

Cyclodextrins are, however, fraught with disadvantages. An ideal cyclodextrin would exhibit both oral and systemic safety. It would have water solubility greater than the parent cyclodextrins yet retain or surpass their complexation characteristics. The disadvantages of the cyclodextrins, however, include: limited space available for the active molecule to be entrapped inside the core, lack of pure stability of the complex, limited availability in the marketplace, and high price.

Microencapsulation is a process by which tiny parcels of a gas, liquid, or solid active ingredient (also referred to herein and used interchangeably with "core material") are packaged within a second material for the purpose of shielding the active ingredient from the surrounding environment. These capsules, which range in size from one micron (one-thousandth of a millimeter) to approximately seven millimeters, release their contents at a later time by means appropriate to the application.

There are four typical mechanisms by which the core material is released from a microcapsule: (1) mechanical rupture of the capsule wall, (2) dissolution of the wall, (3) melting of the wall, and (4) diffusion through the wall. Less common release mechanisms include ablation (slow erosion of the shell) and biodegradation.

Microencapsulation covers several technologies, where a certain material is coated to obtain a micro-package of the active compound. The coating is performed to stabilize the material, for taste masking, preparing free flowing material of otherwise clogging agents etc. and many other purposes. This technology has been successfully applied in the feed-addition industry and to agriculture. The relatively high production cost needed for many of the formulations is, however, a significant disadvantage.

In the cases of nanoencapsulation and nanoparticles (which are advantageously shaped as spheres and hence, nanospheres), two types of systems having different inner structures are possible:

a) a matrix-type system composed of an entanglement of oligomer or polymer units, defined as nanoparticles or nanospheres and b) a reservoir-type system, consisting of an oily core surrounded by a polymer wall, defined as a nanocapsule.

Depending upon the nature of the materials used to prepare the nanospheres, the following classification exists:

a) amphiphilic macromolecules that undergo a cross-linking reaction during preparation of the nanospheres;

b) monomers that polymerize during preparation of the nanoparticles;

c) hydrophobic polymers, which are initially dissolved in organic solvents and then precipitated under controlled conditions to produce nanosparticles.

Problems associated with the use of polymers in micro- and nanoencapsulation include: the use of toxic emulgators in emulsions or dispersions, polymerization or the application of high shear forces during emulsification process, insufficient biocompatibility and biodegrability, balance of hydrophilic and hydrophobic moieties, etc. These characteristics lead to insufficient drug release.

Dendrimers are a class of polymers distinguished by their highly branched, tree-like structures. They are synthesized in an iterative fashion from ABn monomers, with each iteration adding a layer or "generation" to the growing polymer. Dendrimers of up to ten generations have been synthesized with molecular weights in excess of 106 kDa. One important feature of dendrimeric polymers is their narrow molecular weight distributions. Indeed, depending on the synthetic strategy used, dendrimers with molecular weights in excess of 20 kDa can be made as single compounds.

Dendrimers, like liposomes, display the property of encapsulation; being able to sequester molecules within the interior spaces. Because they are single molecules, not assemblies, drug-dendrimer complexes are expected to be significantly more stable than liposomal drugs. Dendrimers are thus considered as one of the most promising vesicles for drug delivering systems. However, dendrimer technology is still in the research stage, and it is speculated that it will take years before the industry will apply this technology as a safe and efficient drug delivery system.

What is needed is a safe, biocompatible, stable and efficient drug delivery system that comprises nano-sized particles of an active ingredient for enhanced bioavailability and which overcomes the problems inherent in the prior art.

SUMMARY OF THE INVENTION

Lipophilic and hydrophilic compounds that are solubilized in the form of nano-sized particles, or "nanoparticles", can be used in pharmacology, in the production of food additives, cosmetics, and agriculture, as well as in pet foods and veterinary products, amongst other uses.

The present invention provides nanoparticles and methods for the production of soluble nanoparticles and, in particular, inclusion complexes of water-insoluble lipophilic and water-soluble hydrophilic organic materials. The present invention also provides an apparatus for producing these soluble nanoparticles using the novel method of production.

Soluble nanoparticles, referred to as "solu-nanoparticles" in accordance with the present invention are differentiated by the use of water soluble amphiphilic polymers that are capable of producing molecular complexes with lipophilic and hydrophilic active compounds or molecules (particularly, drugs and pharmaceuticals). The solu-nanoparticles formed in accordance with the present invention render insoluble compounds soluble in water and readily bioavailable in the human body.

In accordance with the present invention, the solu-nanoparticles are comprised of polymers having an active compound or molecule wrapped and fixated or secured within the polymer. The solu-nanoparticles involve the active compound or molecule, which is linked with the polymer by non-valent bonds and form a polymer-active compound as a distinct molecular entity. The outer surface of the solu-nanoparticles is comprised of a polymer that carries the drug molecule to the target destination. The complex may be nano-level in size, and no change occurs in the drug molecule itself when it is enveloped, or advantageously wrapped, by the polymer. The solu-nanoparticle remains stable for long periods of time, may be manufactured at a low cost, and may, improve the overall bioavailability of the active compound.

The polymer used in the formation of these complexes is selected from the group of amphiphilic polymers that demonstrate hydrophilic-lipophilic balance (HLB) so that the sum total HLB of the complex allows for water solubility with stable solutions of nano-emulsions or nano-suspensions. The amphiphilic polymer is selected using an algorithm that takes into account the molecular weight, the dimensions (in three directions), the surface polarity and the solubility in non-aqueous solvents of the lipophilic or hydrophilic compound. Unlike prior art inclusion complexes, the inclusion complex of the present invention imposes no limitations upon the size of the core compound that can be used. The conditions during the process of forming the nano-soluparticles are such that they do not lead to the destruction of the molecular composition of the core active lipophilic or hydrophilic compound or to the loss of its physiological or biological activity. With regard to the process of preparing the inclusion complexes of the present invention, the process temperature is always lower than the temperature at which the lipophilic compound is losing its physiological or biological activity, or the temperature at which the lipophilic composition changes its chemical composition.

Depending upon the polymer used in the formation of the solu-nanoparticles, drugs and pharmaceuticals as the active compound within the complex, are able to reach specific areas of the body readily and quickly. The polymer and active compound selected will also provide solu-nanoparticles capable of multi-level, multi-stage and/or controlled release of the drug or pharmaceutical within the body.

A significant advantage and unique feature of the complex (inclusion or other) of present invention is that no new bonds are formed and no existing bonds are destroyed during the formation of the inclusion complex. Additionally, existing conditions during the addition of the active compound into the formulation of this complex assures the creation of soluble nanoparticles. Furthermore, the ingredients used in the preparation of the complex are inexpensive, abundant, non-toxic and safe for use in the surrounding environment.

In another aspect of the present invention, a novel chemical reactor apparatus is provided for carrying out the method of forming the solu-nanoparticles in accordance with the present invention. The chemical reactor of the present invention provides for continuous circulation of a "carrier" between the polymer solution and the active compound during the production of the complex of the present invention. This ensures a high uniformity of the emulsion or the suspension formed during the process. The design of the chemical reactor allows all of the processes to occur in the same vessel, thus ensuring high purity in the final product and also simplifying the process and reducing the labor required.

The above description sets forth rather broadly the more important features of the present invention in order that the detailed description thereof that follows may be better understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

BRIEF DESCRIPTION OF THE DRAWINGS

The invention will be better understood by reference to the appended figures in which:

FIG. 3 is a chart comparing the pharmacokinetics constants of the tested clarithromycin in nano-particle complex compared to published data of commercial clarithromycin;

DETAILED DESCRIPTION OF THE INVENTION

Figure 1:
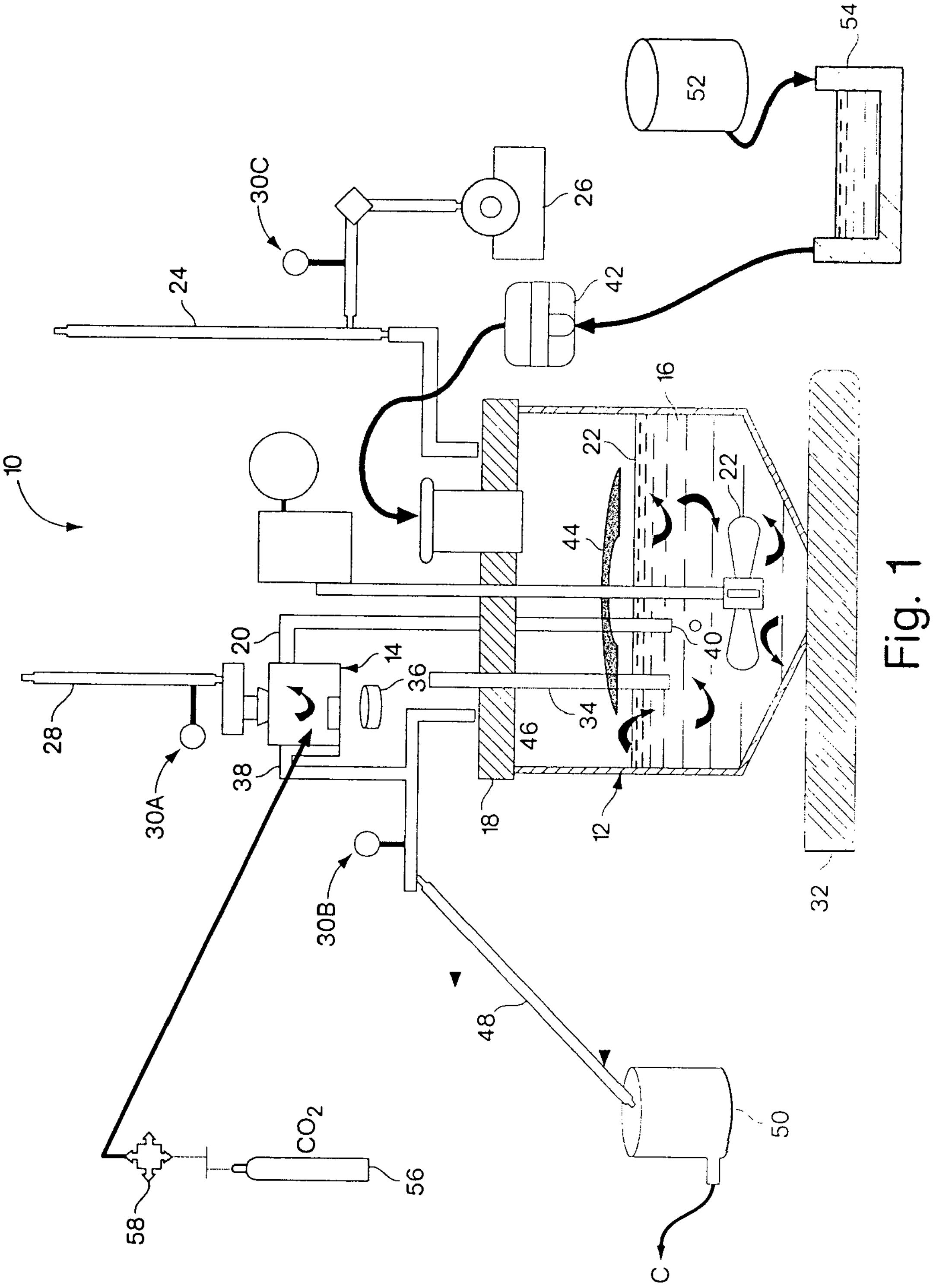
FIG. 1 is a schematic drawing of a chemical reactor for the manufacture of nano-sized soluble particles in accordance with the present invention.

The nanoparticles of the present invention comprises an insoluble or soluble active compound or core, wrapped within a medium soluble amphiphilic polymer. A variety of different polymers can be used for any selected active (lipophilic or hydrophilic) compounds. The polymer, or groups of polymers, is selected according to an algorithm that takes into account various physical properties of both the active lipophilic or hydrophilic compound and the interaction of this compound within the resulting active compound/polymer nano-soluparticle.

As used herein, the terms "lipophil", "lipophilic molecule" and "lipophilic compound" are used interchangeably and are all intended to refer to the same thing. The molecules and compounds referred to herein as lipophilic molecules and lipophilic compounds have a hydrophilic-lipophilic balance (HLB) of less than 6, and fall within the HLB International scale, which ranges from 0–20. Hydrophilic molecules have a hydrophilic-lipophilic balance (HLB) of more than 6. HLB is discussed in greater detail herein below.

More particularly, the ingredients of the composition of the present invention comprise the active (lipophilic or hydrophilic) compound (preferably a lipophil) and the polymer to provide a molecular entity. The lipophil may be any organic molecule or compound that is insoluble in the water and is preferably a drug or pharmaceutical composition. The lipophilic compound can be small or large, simple or complex, heavy or light and may comprise a variety of functional groups. The polymer or polymers used to make up the complex may be selected from the group of polymers approved for human use (i.e. biocompatible and FDA-approved). Such polymers comprise, for example, but are not limited to: natural polysaccharides, polyacrylic acid and its derivatives, polyethylene imine and its derivatives, polymethacrylic acid and its derivatives, polyethylene oxide and its derivatives, polyvinyl alcohol and its derivatives, polyacetylene derivatives, polyisoprene derivatives and polybutadiene derivatives.

As recited, the polymer or groups of polymers used in the formation of the nano-soluparticles of the present invention are selected according to an algorithm that takes into account various physical properties of the active compounds and the polymer or polymers, as well as their future interaction in the resulting complex. The algorithm is utilized in this manner to select the optimal polymer(s) and to assess properties such as pH, ionic force, temperature and various solvent parameters. More specifically, the amphiphilic polymer is selected using the algorithm that assesses the molecular weight, dimensions (in three directions) and the solubility of the lipophilic or hydrophilic compound in non-aqueous solvents. The algorithm also takes into consideration the following properties of the polymer itself in selecting a polymer for the active molecule/polymer interaction in the formation of the complex: molecular weight, basic polymer chain length, the length of the kinetic unit, the solubility of the polymer in water, the overall degree of solubility, the degree of polymer flexibility, the hydrophilic-lipophilic balance, and the polarity of the hydrophilic groups of the polymer.

This system comprises a selected polymer that is soluble in water, and has a hydrophilic-lipophilic balance (HLB) that assures solubility of the complex including the lipophil or hydrophil and the polymer. The carrier is a non-aqueous solvent (or group of solvents) of the water-insoluble lipophilic compound or of the water soluble hydrophilic compound, having a boiling point temperature lower than that of water, and more specifically having a boiling point temperature lower that that of destruction of non-valent bonds creating the complex (at that pressure at which the process of complex creation is being carried out). The creation of the complex does not involve the formation of any valent bonds (which may change the characteristics or properties of the active compound). In the complex of the present invention, weak, non-covalent bonds, such as H-bonds and Van der Waals forces form during the creation of the inclusion complex. The formation of non-valent bonds preserves the structure and properties of the lipophilic compound, which is particularly important when the active compound is a pharmaceutical. As used herein, "non-valent" is intended to refer to non-covalent, non-ionic and non-semi-polaric bonds and/or interactions.

Following the selection of the active compound, a determination is made of its requisite properties for construction of a geometrical model. A polymer suitable for complexation with the given compound is then selected. The main properties of the polymer include its HLB (hydrophilic-lipophilic balance), the length and the flexibility of its polymer chain, and also the state of polarity of the hydrophilic groups. The HLB of the polymer is selected in such a way that after combining to it the active compound the summary HLB of the complex renders the complex soluble. At this stage a geometrical model of the complex is constructed and determination is made of the length of the fragment of the polymer chain needed for the complex. The HLB is calculated following the building of a virtual complex on a computer screen. To this end existing computer programs for animation of molecular structures are used. The HLB can be calculated as a ratio of hydrophilic and lipophilic groups on the surface of the virtual complex. The molecular weight of the complex is easily computed and its geometry is determined. More precisely, total HLB of the complex in accordance with the present invention can be calculated after the virtual construction of the complex on the computer screen of a computer system upon which the aforementioned algorithm has been loaded as software. The algorithm that determines the summary HLB thus plays a major role in the selection of components from which the complex is formed. The parameters and library information pertaining to active compounds and polymer molecules are stored in the computer program for calculation of the summary HLB of the complex to be formed.

A determination of the weight correlation of the "amphiphilic polymer to active molecule" is then made. This determination is essential to the generation of the geometric model. The correlation is made based on the total length of the polymer chain, length of the fragment needed to create the complex, molecular mass of the active compound and molecular mass of the fragment:

Formula:

$$N_c = \frac{M_f \times N_f}{M_l} = \frac{M_f}{M_l} \times \frac{M_p}{M_f} = \frac{M_p\ (\text{g-mol})}{M_l\ (\text{g-mol})}$$

wherein:

$N_c$-the weight ratio of the "amphiphilic polymer to lipophilic compound".

$M_f$-the molecular mass of the polymer fragment.

$M_l$-molecular mass of the lipophilic compound.

$M_p$-molecular mass of the polymer.

$N_f$-the quantity of the polymer fragments capable of participating in the complex creation.

Next, the physical parameters of the water solvent for the polymer are evaluated. At this stage determination is made of the pH required to create the complex, the necessary ionic force and the required carrier for the lipophilic compound. Use of the above components creates optimal conditions for controlling the flexibility of the polymer chain.

The carrier non-aqueous solvent is then selected. The purpose of this solvent to transfer the active compound into a very weak (low concentration) solution such that the molecules of the dissolved compound practically do not react with one another. This solution is then delivered into the zone of reaction in the chemical reactor (discussed in detail infra) for the creation of nano-dispersions, such as a nano-emulsion (having a liquid core material) or nano-suspension (having a solid core material).

As used herein, the term "suspension" generally refers to a dispersion of fine particles in a liquid.

As used herein, the term "emulsion" generally refers to a mixture of two normally unmixable liquids in which one is colloidally suspended in the other (defining a dispersed phase). The particle sizes of the dispersed phase in an emulsion generally lie between a few hundred nanometers and a few tens of micrometers Unlike known processes for the preparation of nano-sized particles where polymers are used for stabilization of the dispersion formed, only some of the aforementioned amphiphilic polymers (with previously calculated hydrophilic-lipophilic balance HLB) are used in these dispersion stabilizations. Additionally, specific conditions are selected for the dynamic three dimensional conformation of the amphiphilic polymer in the dispersion, which serves as the creator of the complex and fixator of the core active compound, as opposed to acting as a viscosifier (i.e., for increasing the viscosity). Previously calculated HLB provides for the necessary solubilization of the active compound.

Specific conditions created for the amphiphilic polymer in the "nano-dispersion" formation, results in two factors: (1) the provision of free rotation of the kinetic segments of the polymer chain around the chemical bonds, thus connecting these segments, and (2) the provision of non-valent interaction of the lipophilic functional groups of the amphiphilic polymer and the lipophilic groups of the compound intended for solubilization. These specific conditions include: the pH parameter of the dispersive medium, the ionic forces of the dispersive medium, the components composition of the dispersive medium, the temperature of the complex formulation, the process duration, and the mechanical components of the process. Each of these specific conditions will be discussed in more detail below.

The pH Parameter of the Dispersion Medium.

If the composition of the amphiphilic polymer includes ionogenic functional groups, the polymer could be soluble or at a pH higher than the iso-electric point (polyacids) or lower than iso-electric point (polybases) depending on the polarity of these groups.

In both of these cases the iso-electric point could be determined with a high degree of accuracy on the curve of "viscosity of the polymer solution-pH of the polymer solution". These two types of polymers could participate in the complex creation only within the pH range where their solutions are viscous liquids. For polymers with non-ionogenic functional groups, the clearly defined iso-electric point does not exist and for this reason these polymers could participate in the complex creation in a wide pH range.

Ionic Force of the Dispersive Medium.

Under the influence of the ions of the water-soluble salts in the polymer solution, the geometry of the amphiphilic polymer chains changes. This factor is used for creation of stereo-specific conditions of non-covalent interaction between lipophilic groups of the polymer and the lipophil itself. Nonetheless, many polymers react so actively on the appearance of the salts (a "salting out" process of the polymer), that it is not always possible to utilize this factor in the reaction of complex creation.

Competition exists between the ions and the polymer for water molecules and the ions take water from the hydrate shells of the polymer. As a result of decreasing hydrate shell, the polymer coils to a globule. The greater the ionic activity, the greater the polymer coiling to the globule.

Components Composition of the Dispersive Medium.

With the help of the composition of the solvents it is possible to flexibly control the geometry of the macromolecules. However, for the purpose of solubility (solubilization) of pharmaceuticals, food additives and cosmetics compounds, only biologically safe solvents, such as glycerol, ethylene glycol and less often ethyl alcohol, iso-butanol and dimethylsulfoxide could be used. Additive solvents decrease the dissolving capacity of water. This is similar to salts addition, i.e. the uncoiled polymeric chain transforming to a loose or compact globule. Thus, options for this methods are limited.

Temperature of the Complex Formation.

With the changes of the temperature of the polymer solution, the hydration conditions of the polymer molecule and accordingly its configuration in the solution drastically changes. With the raising of the temperature, hydration shells surrounding the polymer molecule start to detach and the linear macromolecule starts to take on globular form. At the same time, the flexibility of the macromolecule increases. As a result, additional positive conditions for complex creation are created.

The Process Duration

Because of the non-valent interaction during creation of the inclusion, the limiting phase of the process consists of the diffusion of the lipophilic compounds and macromolecules to each other, for each reaction system exists at a minimum time for complex creation. If less time is allowed, the system remains two-phased. This two-phased nano-dispersion is thermodynamically unstable. The subsequent step of evaporating the carrier leaves particles of the dispersed phase in sizes ranging from 1–1000 nm. The polymer molecule in its solution then covers and entraps the active compounds, creating particles. The carrier is evaporated thus forming stable nanoparticles.

The Mechanical Component of the Process

Mixers, dispersers, homogenizers and other equipment provide maximum dispersing of the active compound in the water-polymer solution and accelerate creation formation of an emulsion or suspension with nano-dimension sized particles in a dispersed phase. An advantageous and novel chemical reactor for forming the nano-emulsion or nano-suspension and the nano-soluparticles complex of the present invention is discussed in detail herein below.

The combined effect of the above conditions aids in achieving specifically selected dimensions and proportions for the complex, the maximum dispersing of the active compound and the optimal conditions for the non-valent interaction of the polymer and these compounds during complex formation.

As recited above, the preparation of the complex in accordance with the present invention requires a number of calculations and procedures to be performed prior to commencing the process of preparing the complex. Some calculations and procedures, which are determined using an algorithm on a computer system, include:

(a) calculating the composition and properties of the components for preparing the complex, which comprises an active compound, an amphiphilic polymer, and carrier solvent;

(b) calculating the weight ratio of the amphiphilic polymer to the active compound;

(c) evaluating the physical parameters of the water solvent for the amphiphilic polymer;

(d) determining the proper non-aqueous solvent;

(e) creating a geometric model of the complex.

The algorithm is not limited to these calculations and may be programmed to make additional calculations and determinations as necessary depending upon the properties and characteristics of the complex to be made.

As recited, the production of the molecular complex consisting of an active compound and an amphiphilic polymer according to the present invention, requires the dispersal of the active compound to nano-particle size. The nano-sized particles assure an almost immediate interaction between the dispersed nano-sized particles of the active compound and the polymer molecules. In accordance with the process of the invention it is also necessary to prevent reverse aggregation (coacervation) of the nano-particles, and to assure an immediate interaction between the dispersed nano-particles of the active compound and the polymer molecules. This assures the formation of a stable complex (inclusion or other). The size of the active compound is determined by constructing its geometrical model (taking into account length of the connections and angles between these connections), and thereafter transferring the compound into a spherical configuration or other geometric shapes. The diameter of this sphere is the deciding measuring size of the active compound. There is a need to take into account that lipophils with long chain structures, as a rule, assume a shape having a globular configuration.

In accordance with the present invention, during the process of forming the soluble nano-sized particle or "solu-nanoparticle", a polymer is added to an aqueous solvent, preferably water, to form a polymer solution in a first vessel of a chemical reactor. Additionally, ingredients may be added to adjust the pH and ionic force level of this solution as needed based on the parameters determined via the algorithm used to select the active compound and polymer. An active compound, which is advantageously an insoluble lipophil, is placed in a second vessel of the chemical reactor. The active compound (or core) may be of any size, dimension or weight, and may comprise any of a variety of functional groups. A solution of the insoluble lipophilic or hydrophilic compound in a non-aqueous solvent (or mixture of solvents) is referred to as the "carrier". The velocity of pouring or adding the carrier to the polymer solution is regulated by one or more regulating taps, which ensure that the lipophil solution being added to the polymer solution has a concentration below 0.1%.

The lipophil solution is formed when the polymer solution is heated and steam from the heated polymer solution condenses and dissolves the lipophil, present in the second vessel. The lipophil solution (in carrier) is then mixed with the polymer solution to form a dispersed phase in emulsion or suspension. Within the chemical reactor, the emulsion is fed into an area of turbulence caused by a disperser (more precisely a nano-disperser) that causes the formation of nano-sized lipophil molecules within the emulsion or suspension. The area of turbulence is referred to as the "action zone" or the "zone of interaction". The emulsion or suspension being fed into the area of turbulence has a Reynolds number of Re>110,000. The emulsion thus becomes a "nano-emulsion" or "nano-suspension" having particles in the range of approximately 1 to approximately 1000 nm. The particle production can also be extended to include small micron sized particles. Within the nano-emulsion or nano-suspension there exists a dispersion medium comprised of the polymer solution, and a dispersed phase comprising the solution of the lipophil in the carrier. This two-phased nano-emulsion or nano-suspension is, however, unstable. Evaporating the carrier leaves particles of the dispersed phase in sizes ranging from approximately 1 to approximately 1000 nanometers. The polymer molecule in the polymer solution then surrounds or envelopes, and more appropriately wraps, the active compounds that had remained in the particles of the dispersed phase after evaporation of the carrier, thus forming a homogeneous nano-sized dispersion of water-insoluble lipophilic compound wrapped by a hydrophilic polymer in an inclusion complex. The remaining carrier is then evacuated by vacuum evaporation or other appropriate drying techniques (e.g., lyophilization, vacuum distillation). As a result of the algorithm used to select the optimal active compound and polymer for the formation of the emulsion or suspension and resulting complex, no free polymer generally remains after the evaporation of the carrier. Following evaporation of the carrier, the stable inclusion complex is comprised of amorphous and/or partially crystalline or crystalline active entities. It is known by those skilled in the art that the amorphous state is preferred for drug delivery as it may indeed enhance bioavailability.

In an advantageous and preferred embodiment of the invention, the polymer molecule in the polymer solution "wraps" the active compound via non-valent interactions (e.g. electrostatic forces, Van der Waals forces, H-bonds) between the polymer and active compound such that the non-valent interactions fixate the active compound within the polymer which thus reduces the molecular flexibility of the active compound and polymer.

The invention further comprises a novel chemical reactor designed for the production of the nano-soluparticles in accordance with the present invention. As illustrated in FIG. 1, the chemical reactor 10 comprises a first vessel 12 and a second vessel 14. In accordance with the present invention, a polymer solution 16 comprised of the selected polymer in water is prepared having a concentration, pH and ionic properties in accordance with previously determined parameters. Distilled water vessel 52 contains distilled water indicated by "W" and is positioned in cover 18. The distilled water in distilled water vessel 52 is transferred to a polymer vessel 54 to which an estimated quantity of the selected polymer is added. This polymer solution formed in polymer vessel 54 is transferred to first vessel 12 via the action of peristaltic pump 42 as indicated by directional arrow "X". Polymer solution 16 is added into first vessel 12 via an opening in cover 18 with the assistance of peristaltic pump 42. A non-aqueous solvent ("carrier") is added to the polymer solution 16 in first vessel 12.

The active compound is added to second vessel 14, which is connected to first vessel 12 via reverse tube 20 so as to permit fluid communication between second vessel 14 and first vessel 12. A carbon dioxide ($CO_2$) balloon 56 with a pressing reducing valve 58 may provide a feed of $CO_2$ gas into second vessel 14. The feed of carbon dioxide acid gas $CO_2$ in an organic solution improves following operational characteristics:

(a) lowering of boiling point of a solvent;

(b) lowering of density of a solvent;

(c) lowering of a thermal capacity of a solvent; and (d) initiation of effect of "explosion" of microdrips of an organic solution hitting in a polymeric solution (cavitation).

Factors (a)–(d) promote faster and complete removal of an organic solvent from a water-polymeric solution. Factor (d) promotes a more complete dividing of microdrips of an organic solution A nano-disperser 22 is positioned within first vessel 12 to create high shear and turbulence in the solution and to effect dispersal of the solution (in the carrier) that enters first vessel 12 from second vessel 14 via reverse tube 20. The nano-disperser 22 creates nano-sized lipophilic particles within the polymer solution 16 in first vessel 12. The nano-disperser 22 is also commonly referred to as a dispergator or homogenizer. A first condenser 24 connected to a vacuum pump 26 extends into first vessel 12. A second condenser 28 is connected to second vessel 14. Taps 30A, 30B, 30C are provided at various locations on the chemical reactor to control first and second condensers 24, 28, as well as to regulate the flow of solutions and vapors between said first vessel 12 and said second vessel 14.

An electrical heater 32 is positioned below first vessel 12 to heat solution 16 therein. First vessel 12 is heated above the boiling point of the carrier, which is lower than the boiling point of polymer solution 16. An electric thermometer 34 extends into first vessel 12 to control and monitor the temperature of solution 16 within first vessel 12. A magnetic mixer and heater 36 is positioned below second vessel 14 to heat and mix the lipophilic compound with the carrier solvent in second vessel 14.

As a result of the heating, the vapors of the non-water solvent (carrier) in first vessel 12 rise up through a steam pipe 38, enter second vessel 14 and condense therein. In second vessel 14, the active compound slowly dissolves in the non-aqueous solvent and the resulting lipophilic solution flows via reverse tube 20 back into the first vessel 12. An opening 40 of reverse tube 20 is arranged in such a way that the lipophilic solution enters first vessel 12 in the area close to the nano-disperser 22, referred to as the "action zone" or "reaction zone", and has a turbulent flow with a Reynolds number of Re>10,000. The Reynolds number is a measurement of the smoothness of flow of a fluid. A high Reynolds number implies that the flow is turbulent, while a low Reynolds number implies that the flow is laminar. The emulsion or suspension is formed here. In the action zone, the nano-disperser operates in the range of approximately 10,000 and up revolutions per minute.

Screen 44 prevents this turbulent flow from entering the air space 46 of the first vessel 12 above the liquid phase. The process is continued until the entire active compound transfers into the polymer solution 16. The non-water solvent is removed from both vessels 12, 14 via cooler 48 into a condensate container 50. The removal of the non-water solvent is illustrated by the arrow indicated by the letter "C". The leftover non-aqueous solvent in first vessel 12 is removed with the assistance of vacuum pump 26. The result is a homogeneous nano-sized dispersion of water-insoluble lipophilic compound wrapped by a hydrophilic polymer in an inclusion complex.

Depending upon the previously determined protocol for a given reaction system regime, the temperature is then lowered to ambient while simultaneously reducing the rotation speed to zero.

In an exemplary embodiment of the present invention, nano-sized soluble particles of macrolide drugs Erythromycin and Clarithromycin were prepared as inclusion complexes in accordance with the present invention and are described further herein in the Examples. The invention is not, however, limited to the formation nano-sized particles of Erythromycin and Clarithromycin. Other pharmaceuticals and classes of drugs are contemplated by the present invention, such as, for example, analgesics, anti-inflammatory agents, anthelmintics, antianginal agents, anti-arrhythmic agents, antibiotics (including penicillins), anticoagulants, antidepressants, antidiabetic agents, antiepileptics, antigonadotropins, antihistamines, antihypertensive agents, antimuscarinic agents, antimycobacterial agents, antineoplastic agents, immunosuppressants, antithyroid agents, antiviral agents, anti-neoplastic agents and chemotherapeutic agents, anxiolytic sedatives (hypnotics and neuroleptics), astringents, beta-adrenoceptor blocking agents, blood products and substitutes, cardiacinotropic agents, contrast media, corticosterioids, cough suppressants (expectorants and mucolytics), diagnostic agents, diagnostic imaging agents, diuretics, dopaminergics (antiparkinsonian agents), haemostatics, immunosuppressive cyclic oligopeptides, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anorexics, sympathomimetics, thyroid agents, vasidilators and xanthines. Preferred drug substances include those intended for oral administration, intravenous administration, mucosal administration and pulmonary administration. A description of these classes of drugs and a listing of species within each class can be found in Martindale, The Extra Pharmacopoeia, Twenty-Ninth Edition, The Pharmaceutical Press, London, 1989.

Although the present invention has been described with reference to use in the human body, the invention is not limited in this respect and inclusion complexes can be formed in accordance with the present invention for use in veterinary pharmaceuticals and other products as well.

EXAMPLES

Example 1

Experimental Procedure for the Production of the Inclusion Complex

A. Preparation of Polymer Solution.

500 ml of distilled water are transferred from distilled water vessel 52 to polymer vessel 54. To polymer vessel 54 is added an estimated quantity of polymer, which was chosen for creation of Inclusion Complex with lipophilic compound. At temp. 20–25° C. the contents of polymer vessel 54 is mixed at velocity of 30–60 $min^{-1}$ (rotation/min). up to complete dissolution of the polymer and creation of transparent or opalescent solution.

B. Loading Compounds in the Reactor

The polymer solution, prepared in polymer vessel 54 is transferred into first vessel 12 by pump 42. In the same vessel the carrier solvent is loaded. Lipophilic compound is placed into second vessel 14.

C. Starting the Reactor

The nano-disperser 22 is activated at velocity 500–800 $min^{-1}$. The cooling water is entered into first and second condensers 24 and 28. The heater (thermostat) 32 is activated for temperature 5–10° C. above the boiling point of carrier solvent. The magnetic mixer 36 is activated at velocity 5–10 $min^{-1}$.

D. Synthesis of the Complex

After reaching the designated temperature, the carrier solvent starts evaporation from first vessel 12. Its vapor reaches second vessel 14 through steam pipe 38. At this moment the nano-disperser 22 is accelerated to a velocity of 8,000–10,000 $min^{-1}$. The solution of active compound in the carrier solvent then moves from second vessel 14 to first vessel 12 through reverse tube 20. The solution exits through opening 40 and reaches to the zone of the most active action of nano-disperser 22. The temperature in the heater 32 is raised another 5–10° C. in order the concentration of active compound in the carrier solvent remained within the range 0.02–0.1%. The process lasts until all lipophilic compound passes from second vessel 14 to first vessel 12.

E. Removing the Carrier Solvent

The velocity of the nano-disperser reduced to 200–300 $min^{-1}$. Tap 30A is opened on the conduit connecting first vessel 12 with cooler 48 and condensate container 50. The carrier solvent is distilled off to condensate container 50. After the solvent is transferred, tap 30A is closed together with tap 30B on cooler 28. Tap 30C, which is positioned on the conduit connecting first vessel 12 with vacuum-pump 26, is then opened. The temperature in the heater 32 is then reduced to 30–35° C., the vacuum-pump 26 is activated and the remnants of the solvent are evacuated for 1–2 hours. The vacuum-pump 26 is then deactivated, all taps 30A, 30B and 30C are opened and the velocity of the nano-disperser is reduced to 30–60 $min^{-1}$.

F. Completing the Experiment

The solution of the inclusion complex is taken from first vessel 12 and was analyzed. The results are indicated in table 1.

TABLE 1

Combination of water-phase, polymer, and active compound and the process temperature used for the preparation of selected nano-emulsions or nano-suspensions and their stability (pre-formulation level) determined via length of time (days).

| Solvent (water phase) | Polymer | Carrier | active compound | Process Temp (° C.) | Stability (days) |
|---|---|---|---|---|---|
| Water + 0.9% NaCl | Carragenan | Hexane | Vaseline(Oleum vaselini), hydrocarbons' mixture | 65 | 30 |
| Solvent "Quartasolum" (NaCl, KCl, $NaHCO_3$, $CH_3COONa$) | Xantan | Diethyl ether | Nut oil & almond oil (Oleum Amigdalarum) 1:1, aromatic esters' mixture, triglycerides, aromatic nitriles and vitamins | 60 | 300 |
| Distilled water + ethanol (10%) | Polyacryl-amide | Diethyl ether | Oregano oil, phenols and polyphenols, complicated aromatic esters' mixture | 55 | 100 |
| Distilled water + glycerol (10%) | Starch | Benzene | Simethicone, olygo(dimethylsiloxan)s mixture (Antifoaming medication) | 70 | 30 |
| Solvent "Quartasolum" | Agar-agar | Diethyl ether | Pine Oil (raw material for Camphora), mixture of camphora, turpentine and other terpens and terpenoids | 60 | 100 |

Example 2

Modification of Polysaccharide

Distilled water with polysaccharide in varying amount was put into the vessel. After that a citric acid was added until the designated pH 2 at mixing was attained. X1 signifies the amount of polysaccaride in water, X2 signifies the pH value of water solution of polysaccharide The obtained suspension is heated for approximately 10–20 minutes with continuous mixing at room temperature up till to 70–95 degrees ° C. up till a homogeneous opaque mass is obtained. The obtained mass is put in an autoclave on time X3 and exposed in an autoclave at temperatures 160–180° C. Under these conditions the network structures of a polysaccharide partially or completely are transformed to linear weakly branched macromolecules and which dissolve in water. Upon termination of the autoclave time the cooling below 100° C. is effected and a solution of polymer is obtained. A solution of polyethylene glycol—400 (PEG-400) in an amount X4 (% in relation to polysaccharide) is added. The obtained mixture is put in an autoclave and heated up a temperature of 160–180° C. during time X5. At the end of the autoclave time cooling below 100° C. is effected and the modified polymer is obtained. Turbidity and viscosity of the solution were measured. The observed data is shown in table 2.

TABLE 2

Modified starch based on potato starch

| C p. st., % $X_1$ | pH $X_2$ | $T_{1\ min}$ $X_3$ | PEG-400, $X_4$ % | $T_{2\ min}$ $X_5$ | Turbidity FTU |
|---|---|---|---|---|---|
| 4 | 2 | 30 | 0 | 0 | 370 |
| 4 | 2 | 40 | 0 | 0 | 310 |
| 4 | 2 | 50 | 0 | 0 | 245 |
| 4 | 2 | 60 | 0 | 0 | 190 |
| 4 | 2 | 80 | 0 | 0 | 145 |
| 4 | 2 | 100 | 0 | 0 | 95 |
| 4 | 2 | 120 | 0 | 0 | 63 |
| 4 | 2 | 150 | 0 | 0 | 26 |
| 4 | 2 | 180 | 0 | 0 | 4 |
| 8 | 2 | 150 | 0 | 0 | 65 |
| 4 | 2 | 30 | 25 | 40 | 272 |
| 4 | 2 | 40 | 50 | 40 | 14 |

TABLE 2-continued

Modified starch based on potato starch

| C p. st., % $X_1$ | pH $X_2$ | $T_{1\ min}$ $X_3$ | PEG-400, $X_4$ % | $T_{2\ min}$ $X_5$ | Turbidity FTU |
|---|---|---|---|---|---|
| 4 | 2 | 40 | 50 | 60 | 21 |
| 4 | 2 | 30 | 75 | 60 | 7 |
| 4 | 2 | 50 | 75 | 40 | 4 |
| 4 | 3 | 30 | 25 | 60 | 126 |
| 4 | 3 | 50 | 25 | 40 | 130 |
| 4 | 3 | 50 | 75 | 60 | 143 |
| 4 | 3 | 30 | 75 | 40 | 400 |
| 4 | 3.5 | 40 | 25 | 60 | 129 |
| 4 | 3.5 | 60 | 25 | 45 | 100 |
| 4 | 3.5 | 40 | 25 | 90 | 63 |
| 8 | 2 | 150 | 0 | — | 270 |
| 8 | 2 | 150 | 50 | 60 | 210 |
| 4 | 2 | 150 | 50 | 60 | 71 |
| 4 | 3 | 40 | 100 | 40 | 7 |
| 4 | 2 | 40 | 100 | 40 | 4 |
| 4 | 2 | 50 | 25 | 60 | 3 |
| 4 | 2 | 80 | 75 | 60 | 23 |

Example 3

Creation of Solu Nano-particles Wrapped in Modified Polysaccharide (Parts by Weight)

In distilled water a polysaccharide is dissolved, initially heated at 160–180 degrees C. up to molecular masses (5–10)×10(4) and is modified by the polyethylene glycol PEG-400. Conditions of modification: ratio "polysaccharide—polyethylene glycol PEG-400" ratio from 2:1 up to 4:1, acidic environment with pH 2–5 created by a citric acid, temperature 160–180° C., time of modification 60–180 min. Solution of a modified polysaccharide is put in a reactionary vessel, heated up to 60° C. mixing by a homogenizer at speed 10,000 and up rev/min.

Simultaneously a solution of macrolide in an organic solvent is prepared. Allowing the solution of a polysaccharide to reach given temperature 60° C., then it start to add a solution of macrolide with speed about 1 ml/sec. Speed of a homogenizer is increased to 10 thousand rev/min and up. The macrolide interacts with the polymer creating nanoparticles, and the organic solvent is evaporated. The organic solvent is condensed in a direct condenser. After all the macrolide has entered interaction with the polymer and has solubilized as an inclusion complex "macrolide-polymer", the organic solvent was vacuum evaporated with continuous mixing, and the solution of the complex was cooled to 30–35° C.

Turbidity (table 3) and viscosity are measured in the cooled solution. The presence of a crystalline phase and particles sizes of the complex were measured

TABLE 3

Complexes with Clarithromycin

| Product number | Solution components | Store Time (days) | Turbidity (FTU) at room temperature |
|---|---|---|---|
| 39 | Hydrolyzed polysaccharide - 5%, clarithromycin - 1%, pH 5.0 | 0 | 29 |
| | | 4 | 27 |
| | | 10 | 35 |
| | | 20 | 28 |
| | | 26 | 30 |

TABLE 3-continued

Complexes with Clarithromycin

| Product number | Solution components | Store Time (days) | Turbidity (FTU) at room temperature |
|---|---|---|---|
| 37 | Hydrolyzed polysaccharide - 4%, Clarithromycin - 2%, pH 4.5 | 0 | 38 |
| | | 5 | 40 |
| | | 21 | 36 |
| | | 27 | 43 |
| 40 | Hydrolyzed polysaccharide - 4%, Clarithromycin - 2%, pH 5.5 | 0 | 36 |
| | | 1 | 36 |
| | | 7 | 37 |
| | | 17 | 36 |
| 42 | Hydrolyzed modified (50% PEG) polysaccharide - 6%, clarithromycin - 1%, pH 4.5 | 0 | 40 |
| | | 1 | 40 |
| | | 6 | 39 |
| | | 16 | 41 |
| | | 22 | 40 |
| 34 | Hydrolyzed modified (25% PEG) polysaccharide - 3.75%, clarithromycin - 1%, pH 4.5 | 0 | 21 |
| | | 10 | 20 |
| | | 16 | 19 |
| | | 26 | 20 |
| 36 | Hydrolyzed modified (50% PEG) polysaccharide - 6%, clarithromycin - 1.5%, pH 5.0 | 0 | 46 |
| | | 15 | 48 |
| | | 21 | 47 |
| | | 30 | 49 |
| 38 | Hydrolyzed modified (30% PEG) polysaccharide - 5.2%, clarithromycin - 1.7%, pH 5.5 | 0 | 26 |
| | | 4 | 28 |
| | | 10 | 27 |
| | | 20 | 26 |
| 43 | Hydrolyzed modified (50% PEG) polysaccharide - 12%, clarithromycin - 2.5%, pH 6.5 | 0 | 38 |
| | | 1 | 37 |
| | | 5 | 39 |
| | | 15 | 37 |
| | | 25 | 38 |
| 46 | Hydrolyzed modified (50% PEG) polysaccharide - 6%, clarithromycin - 2.5%, pH 5.0 | 0 | 36 |
| | | 1 | 40 |
| | | 3 | 44 |
| | | 9 | 48 |
| | | 10 | 50 |
| | | 17 | 47 |
| 47 | Hydrolyzed polysaccharide - 3.75%, clarithromycin - 1.5%, pH 4.5 | 0 | 32 |
| | | 1 | 31 |
| | | 6 | 35 |
| | | 14 | 32 |
| 48 | Hydrolyzed polysaccharide - 3%, clarithromycin - 1.5%, pH 5.0 | 0 | 25 |
| | | 1 | 25 |
| | | 2 | 26 |
| | | 8 | 25 |
| 50 | Hydrolyzed polysaccharide - 8%, clarithromycin - 1%, pH 5.0 | 0 | 70 |
| | | 1 | 77 |
| | | 4 | 79 |
| | | 6 | 78 |
| 51 | Hydrolyzed modified (25% PEG) polyssacharide - 5%, clarithromycin - 3%, pH 5.0 | 0 | 64 |
| | | 1 | 62 |
| | | 2 | 65 |
| | | 3 | 61 |
| | | 10 | 64 |

Stable Turbidity = stable nano-dispersion.

Example 4

Figure 2:
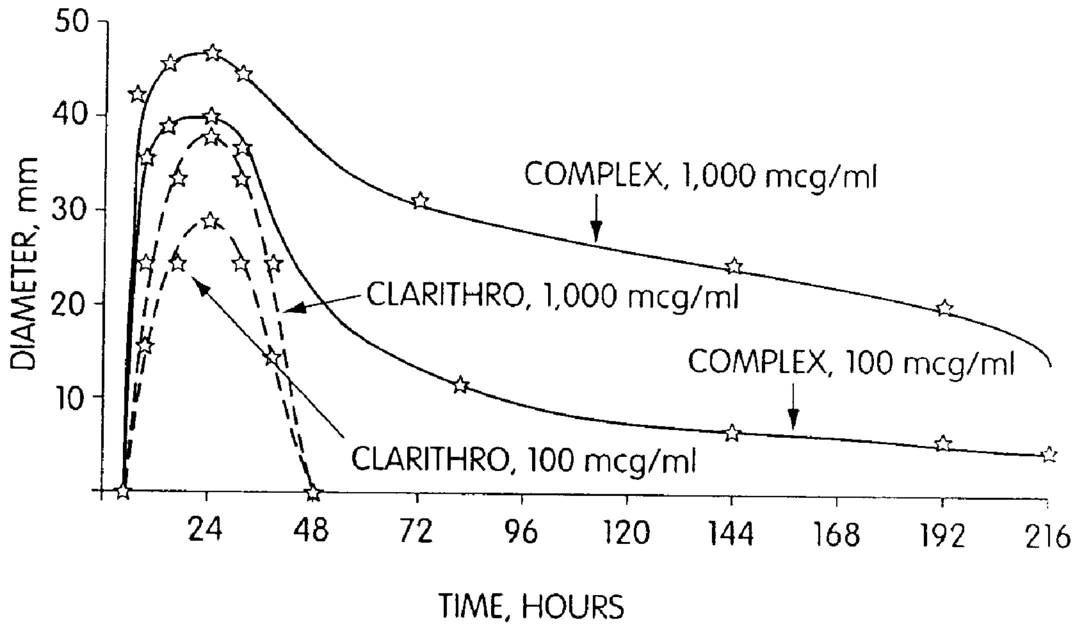
FIG. 2 illustrates the concentrations for both control and complexed clarithromycin testing material observed until 216 hours post application.

In Vitro Microbiologial Results with Clarithromycin in Nano-Particle Complex The microbiological activity of complexed Clarithromycin prepared in Example 5 at various concentrations were tested and compared directly to un-complexed Clarithromycin at the same concentrations. The testing method used was that of the accepted agar-filled petri-dish tests. The test microbe used was *Micrococcous luteus*, which is sensitive to macrolide antibiotics. Small filter paper cut discs were impregnated with specific solution concentrations of the tested antibiotics. Diameters of the zones of bacteriostatic activity were measured versus time. Concentrations were varied significantly for both control and complexed testing material and observed until 216 hours post application. These results are illustrated in FIG. 2.

This test further demonstrated that the complexed clarithromycin shown to have the same microbiological activity as commercial clarithromycin while using 1/10 of the amount (concentration). Furthermore, for identical concentrations of drug, the Clarithromycin microbiological activity ceased at approximately 48 hours, while that of the complexed Clarithromycin continues significantly till approximately 216 hours of current measurements and we are continuing measurements. while that of the complexed Clarithromycin continued significantly until approximately 216 hours of current measurements. It was also observed that the difference in microbiological activity for complexed Clarithromycin having concentration differences of an order of magnitude between them is vastly greater than the corresponding differences noted with Clarithromycin alone.

Example 5

In vivo Studies with Clarithromycin Inclusion Complex

Rats received clarithromycin in nano-particle complex according to the present invention by gavages 150 mg/kg. Blood samples were collected in time intervals through the jugular catheter.

Values of time 0 were the control baseline for each animal. Following oral administration of clarithromycin in nano-particle complex, it was determined that the drug reached its maximum plasma value 4 hours following administration. The first absorption phase was rapid—up to 1 hour and continued until maximum at 4 hours. The clearance was significantly slow in comparison to published data with the commercial clarithromycin. The circulating half-life was in the range of 2 hours. The Area Under the Curve ($AUC_{0\text{-}24hours}$) of the clarithromycin complex in accordance with the present invention was significantly higher 54.2 microg*h/ml in comparison to published data with the same dose of the commercial Clarithromycin in rats $AUC_{0\text{-}24hours}$=32.54 microg*h/ml with same oral dose of 150 mg/kg. It is thus believed that: complexed clarithromycin in accordance with the present invention exhibits either enhanced bio-availability or intestinal slow release following oral administration.

The clarithromycin complex exhibited the same range of circulating half-life i.e., 2 hours in comparison to the commercial drug following IV bolus administration. It possesses a significant higher AUC after oral administration support the assumption of bioavailability enhancement or slow release properties.

Figure 4:
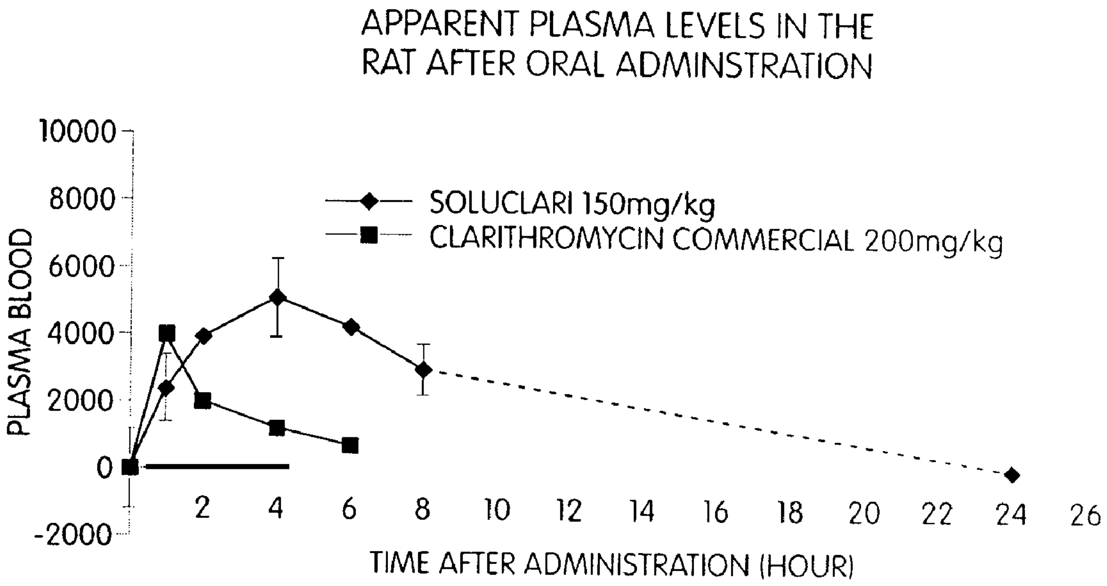
FIG. 4 is a chart comparing the PK constants of clarithromycin in nano-particle complex with published studies with commercial clarithromycin.

A comparison of the pharmacokinetics constants of the tested clarithromycin in nano-particle complex compared to published data of commercial clarithromycin is illustrated in FIG. 3. PK constants of clarithromycin in nano-particle complex in comparison with published studies with commercial clarithromycin is illustrated in FIG. 4.

Example 6

Physical Measurements and Characteristics of Clarithromycin and Erythromycin in Nano-Particle Complex 1. Particle Size and Distribution Complexes of Erythromycin or Clarithromycin plus polymer in aqueous solutions have shown that the technology of the present invention allows the creation of drug-polymer dispersions with controllable nano-particle sizes, ranging from single nanometers up to 1000 nm, with a highly uniform size distribution.

Figure 5:
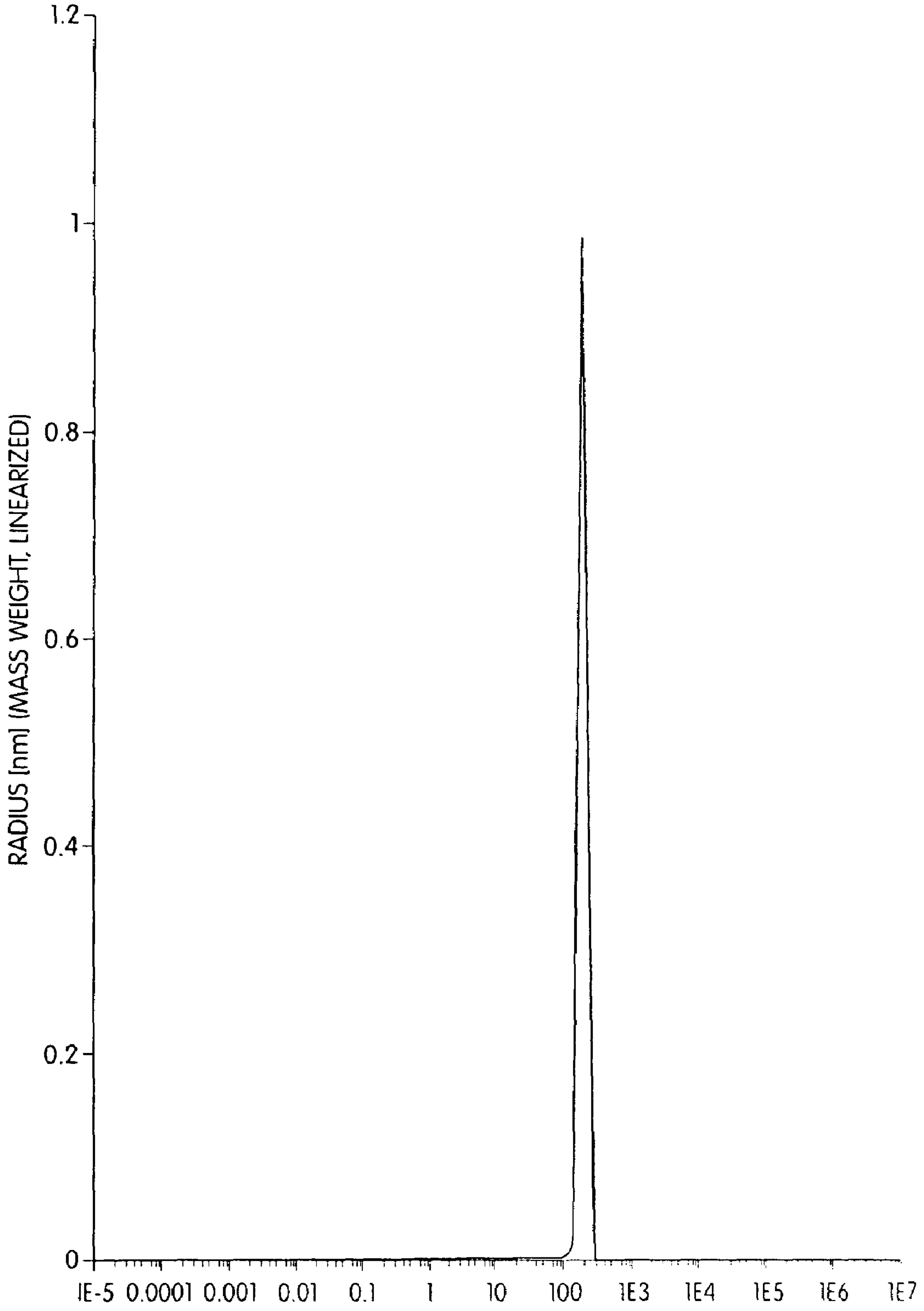
FIG. 5 illustrates a complexed Clarithromycin particle having a size of approximately 190 nm.
Figure 6:
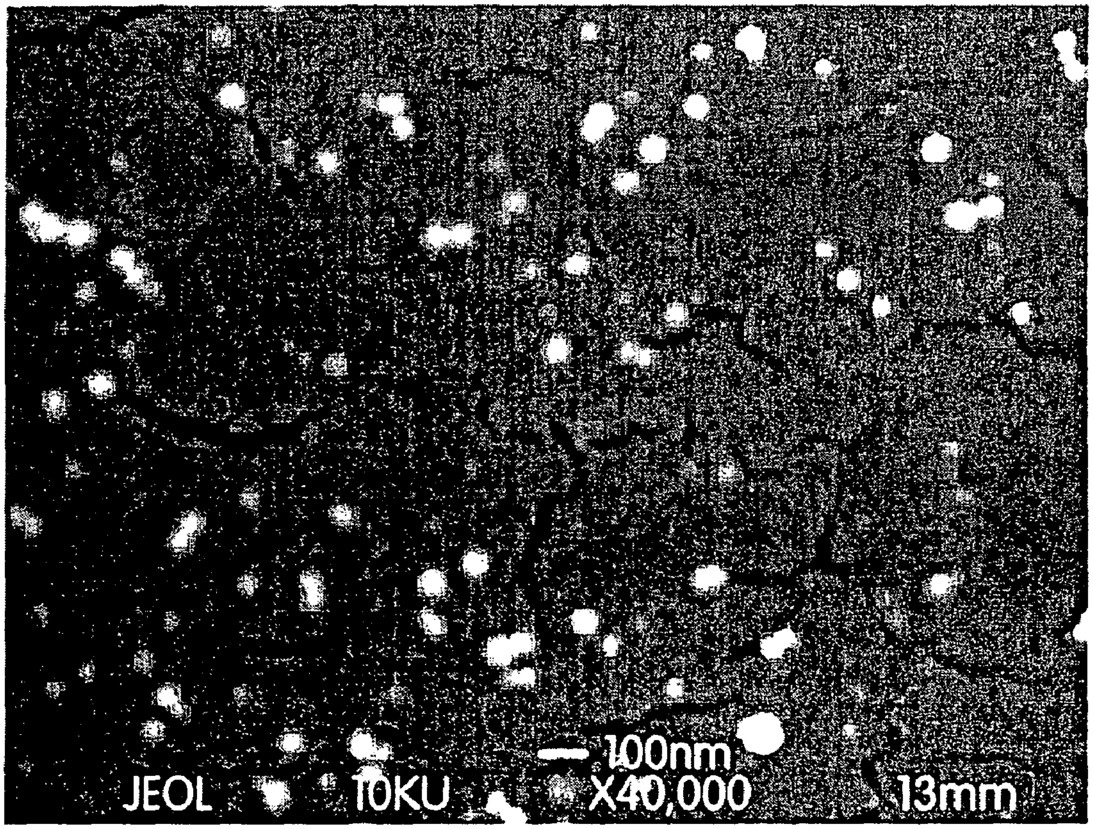
FIG. 6 is an SEM micrograph illustrating the consistent spherical complexed Clarithromycin particles prepared according to the method of the present invention.

A complex of Clarithromycin prepared according to the method of the present invention showed identical dispersion spectra after 5 weeks time. FIG. 5 illustrates a complexed Clarithromycin particle having a size of approximately 190 nm. Size measurements of the Erythromycin and Clarithromycin complexes have been performed using "ALV-Particle Sizer", which has a resolution of from 3–3000 nm. FIG. 6 is an SEM micrograph illustrating the consistent spherical complexed Clarithromycin particles prepared according to the method of the present invention.

2. Solubility

Figure 7:
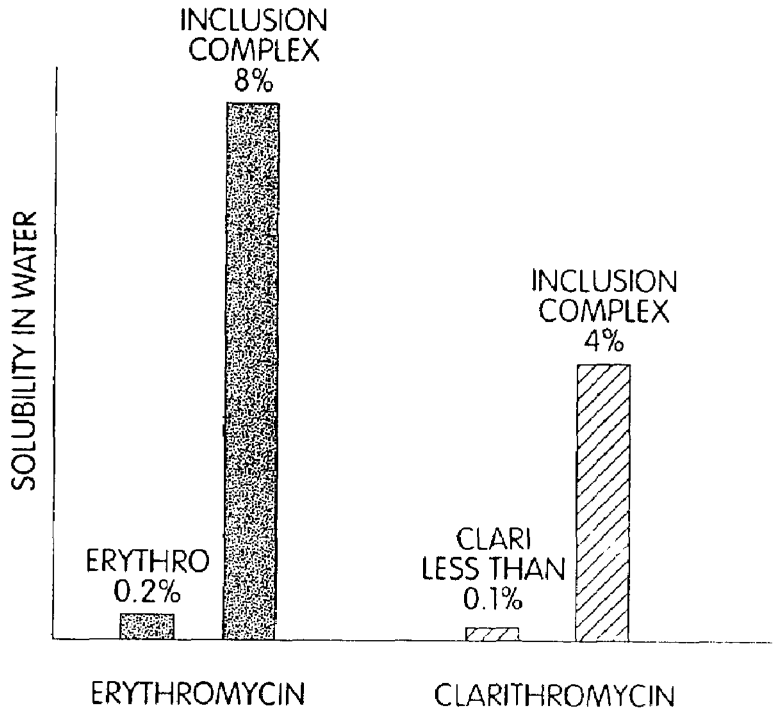
FIG. 7 illustrates the comparison of the solubility of Erythromycin and Clarithromycin alone and as part of the inclusion complex in accordance with the present invention.

Erythromycin, an antibiotic practically insoluble in water, has been reformulated into thermodynamically stable nano-dispersions, with controllable size distribution of the particles in the dispersed phase. The resulting new formulation has 8% (w/v) active drug, which is 40 times higher than the solubility of the original drug in water (0.2%). Moreover, drug particles with a highly uniform size of complexes (over 95%) were achieved. The erythromycin was released from the inclusion complex in sufficient concentration under physiological conditions. No existing technologies of solubilization were used, e.g. surfactants, liposome, capsulation, etc. A comparison of the solubility of Erythromycin and Clarithromycin alone and as part of the inclusion complex in accordance with the present invention is illustrated in FIG. 7.

3. Stability

Observations were made of transparent aqueous solution of inclusion complexes for non-occurrence of phase separation and maintenance of particle size and size distribution. The following observations and results were obtained:

(a) Over the 75 days, the tests of the reformulated 8% Erythromycin showed no phase separation and maintenance of particle size and size distribution.

(b) The stability of the complexed Clarithromycin in accordance with the present invention was observed for 12 weeks at room temperature and 4 weeks at 35° C. and they found to be stable.

(c) Freeze-drying and subsequent rehydration of complexed Clarithromycin, retained particle size of the drug-polymer complexes. For more than 30 days there was no aggregation and the nano-dispersion were stable.

4. X-Ray Diffraction Results and Characterizations

From the X-ray diffraction measurements it was found that the reformulation of the crystalline drug Erythromycin into nano-dispersions was accompanied by its conversion into an amorphous form material.

Figure 8:
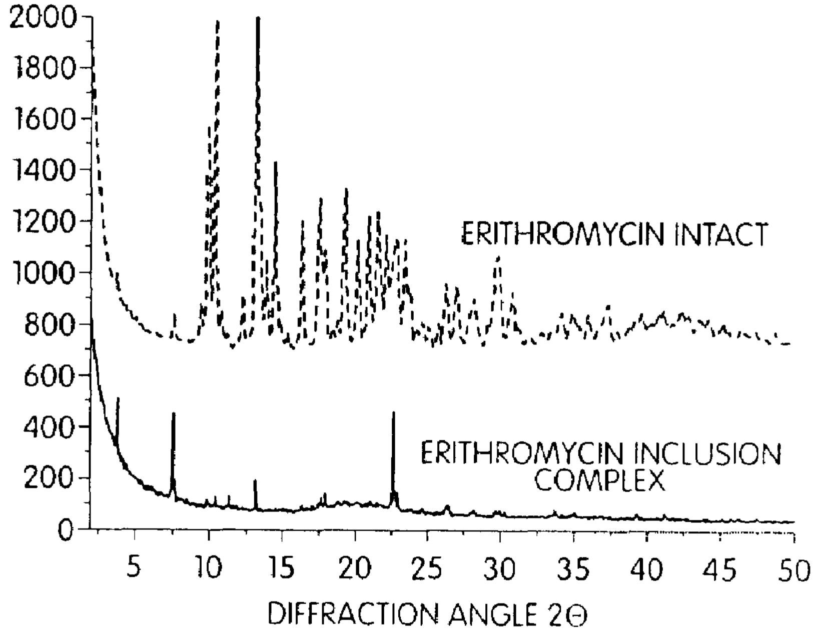
FIG. 8 illustrates the X-ray diffraction comparison of intact Erythromycin compared with the inclusion complex of Erythromycin in accordance with the present invention.
Figure 9:
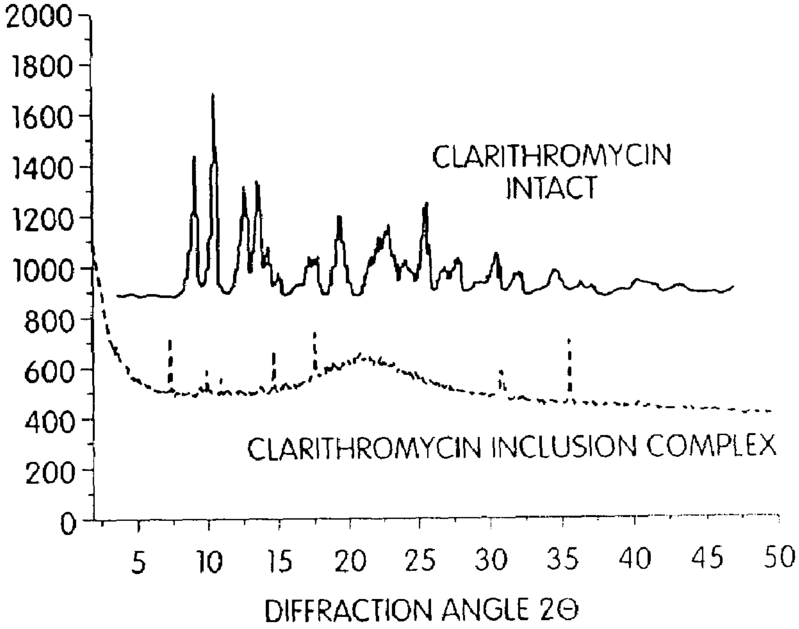
FIG. 9 illustrates the X-ray diffraction comparison of intact Clarithromycin compared with the inclusion complex of Clarithromycin in accordance with the present invention.

FIG. 8 and FIG. 9 illustrate the X-ray diffraction comparisons of intact Erythromycin and intact Clarithromycin compared with the inclusion complex of Erythromycin and Clarithromycin respectively in accordance with the present invention.

The comparison of known spectra of Erythromycin (FIG. 8) and Clarithromycin (FIG. 9) with inclusion complexes in accordance with the present invention were conducted. The known spectrum of Erythromycin (FIG. 8) as a dry powder shows a well-defined crystalline pattern.

In comparison, the Erythromycin inclusion complex (FIG. 8) demonstrates that the majority of peaks derived from crystalline Erythromycin are not present, and the few remaining peaks have been drastically reduced in height. This spectrum is undoubtedly related to that of the known Erythromycin, however it is indicative that another "form" is now present after complexation.

When observing the average scattering angles in the spectra of both complexed Erythromycin and Clarithromycin one can clearly see that certain peaks have been "flattened" showing widened virtually base line peaks. This phenomenon is indicative of an amorphous state.

These results show that complexation of Erythromycin and Clarithromycin using the technology of the present invention reduces crystallinity of the uncomplexed drugs, as the crystal lattices are unable to form, due to fixation of the drugs within the inclusion polymer on the basis of Van der Waals and hydrogen bonds. It is known that the amorphous state is preferred for drug delivery as it may indeed enhance bioavailability.

Figure 10:
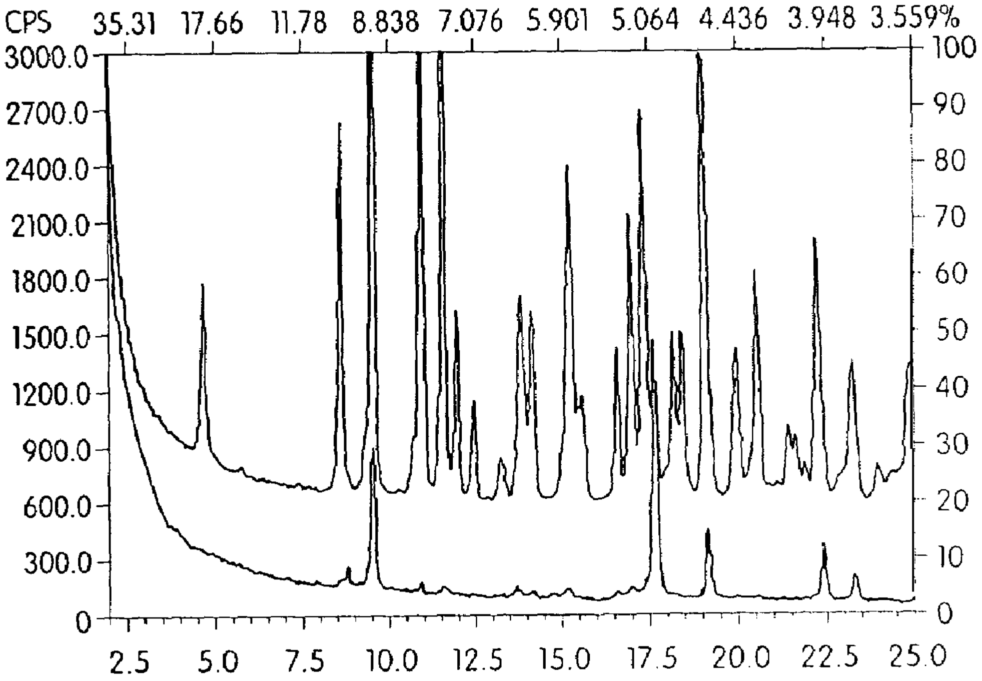
FIG. 10 is an X-ray spectrum of 6 month old clarithromycin complexed sample (bottom trace) compared to the commercially available Clarithromycin (upper trace).

The X-ray spectrum of FIG. 10 depicts a 6 month old clarithromycin complexed sample (bottom trace) compared to the commercially available Clarithromycin (upper trace). This specific complexed sample is identical to that appearing in FIG. 9 and in the microbiological tests discussed in Example 6. This validates the technological ability to prepare uniquely complexed drug conjugates in accordance with the present invention that demonstrate significantly stabilized amorphous states.

The present inventors believe that such stabilization of amorphous or partially amorphous drug states within the inclusion complex may well increase the chances of greater bioavailability as has been documented in the literature. Taken together with other parameters attained using the process and apparatus of the present invention, such as very accurate size control, the process lends itself easily to significantly increased bioavailabilities.

Example 7

Controlled Release from the Erythromycin Inclusion Complex

Reformulation of the drug in inclusion complexes represents a new avenue to achieve controlled release systems that would deliver the drug at a specific rate and pattern. To examine the experimental controlled release pattern of Erythromycin from the inclusion complex, a dialysis method was been performed. In this method, the drug-polymer nano-dispersions were placed within a dialysis membrane bag. Such a membrane allows the diffusion of only molecules and ions of sizes less than 3000 Da, while maintaining the nano-dispersions. Dialysis was performed for 24 hours at a room temperature and with a constant stirring. Samples from the external buffer were taken periodically for the analysis of drug release. The concentration of Erythromycin released from the Inclusion Complex was detected by measuring the O.D. (optical density). After 24 hours of incubation, the concentration of Erythromycin in the external fluid was 25% of the initial concentration of Erythromycin in the inclusion complex (initial concentration is 4 mg/ml (8% w/v)). The released concentration also reflects the maximum solubility of erythromycin in a serum-modeled solution. Thus, this result indicates that the nano-dispersion has a capability to sustain the release of Erythromycin.

Example 8

In vitro Human Cellular Compatibility Study

Erythrocytes were separated from WBC of a fresh donor, and suspended in isotonic buffer. In a water and lyses buffer treatment erythrocytes were suspended in the indicated buffer. Hemolytic reactions were carried at 37° C. with shaking (40 rpm) in a total volume of 1 ml. An aliquot of 250 μl was removed at 4 hr, and the rest was collected at 18 hr. Aliquots were centrifuged at 250 g for 5 min., and supernatant was read at 540 nm. The results of this test found the complexed Clarithromycin to be compatible with human blood.

Example 9

Suspension Polymerization in Nano-soluparticles

Using the chemical reactor of the present invention as illustrated in FIG. 1, caprolactam is dissolved in ethyl ether. An amylose was modified by Urea up to an amidation degree 10% and after that a solution of a modified amylose was prepared. The polymer solution was transferred into first vessel 12 and the caprolactam solution was transferred into second vessel 14. Nano-disperser 22 and heater 32 were activated. The heater (thermostat) 32 was activated for 50–55° C. Caprolactam solution was then transferred from second vessel 14 to first vessel 12 through reverse tube 20. After the all caprolactam solution was fed through reverse tube 20, the temperature of the reaction mixture was reduced to 25–35° C. and evaporated from the reactor.

At the polymerization of Polycaprolactam (nylon-6,6) the obtained "solution" is sprayed in a vacuum column with temperature 260–280° C. Polymer as fine homogenous powder (with uniform size of particles) is taken from the bottom of the string. A molecular weight of polymer is determined by a viscosity method.

The results are indicated in table 4.

TABLE 4

| Concentration of Caprolactam in ethyl ether (%) | Caprolactam Solution (g) | Concentration of Amylose modified in water (%) | Amylose solution (g) | Speed of homogenizer (rev/min) | Interaction time | MW |
|---|---|---|---|---|---|---|
| 2 | 2,000 | 4 | 250 | 20,000 | 150 | 120 |
| 3 | 1,300 | 4 | 250 | 18,000 | 115 | 100 |

TABLE 4-continued

| Concentration of Caprolactam in ethyl ether (%) | Caprolactam Solution (g) | Concentration of Amylose modified in water (%) | Amylose solution (g) | Speed of homogenizer (rev/min) | Interaction time | MW |
|---|---|---|---|---|---|---|
| 4 | 1,000 | 4 | 250 | 12,000 | 80 | 90 |
| 5 | 800 | 4 | 250 | 16,000 | 60 | 90 |

EQUIVALENTS

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is to be understood that the drawings are not necessarily drawn to scale, but that they are merely conceptual in nature.

What is claimed is:

1. A hydrophilic dispersion, comprising a water-insoluble or water soluble active compound and an amphiphilic polymer which wraps said active compound to form a water-soluble nano-sized molecular entity in which non-valent bonds are formed between said active compound and said amphiphilic polymer such that said bonds fixate said active compound within said polymer, in which nano-sized molecular entity the active compound is in the amorphous or partially crystalline state and wherein said amphiphilic polymer does not form rigid matrices nor cross-linked polymers.

2. The hydrophilic dispersion as recited in claim 1, wherein said non-valent bonds include electrostatic forces, Van der Waals forces and hydrogen bonds.

3. The hydrophilic dispersion as recited in claim 1, wherein said amphiphilic polymer is selected from the group consisting of: natural polysaccharides, modified polysaccharides, polyacrylic acid, polyethylene imine, polymethacrylic acid, polyethylene oxide, polyvinyl alcohol, polyacetylene, polyisoprene and polybutadiene.

4. The hydrophilic dispersion as recited in claim 1, wherein said active compound is selected from the group consisting of: peptides, polypeptides, nucleotides and co-ferments, vitamins, steroids, porphyrins, metal-complexes, purines, pyrimidines, antibiotics and hormones.

5. The hydrophilic dispersion as recited in claim 1, wherein said active compound is a pharmaceutical compound.

6. The hydrophilic dispersion as recited in claim 5, wherein said pharmaceutical compound is a chemotherapeutic agent or an antibiotic agent.

7. The hydrophilic dispersion as recited in claim 1, wherein said nano-sized molecular entity is in the range of from approximately 10 to approximately 1000 nanometers in size.

8. A hydrophilic dispersion, comprising a water-insoluble or water soluble active compound and an amphiphilic polymer which wraps said active compound to form a water-soluble nano-sized molecular entity in which non-valent bonds are formed between said active compound and said amphiphilic polymer and said active compound is in the amorphous or partially crystalline state and wherein said molecular entity is an inclusion complex.

9. Nano-sized paraticles comprising a water-insoluble or water soluble active compound in an amorphous or partially crystalline state wrapped within an amphiphilic polymer such that non-valent bonds are formed between said active compound and said amphiphilic polymer, and said amphiphilic polymer does not form rigid matrices or cross-linked polymers.

10. The nano-sized particles as recited in claim 9, wherein said non-valent bonds include electrostatic forces, Van der Waals forces and hydrogen bonds.

11. The nano-sized particles as recited in claim 9, wherein said active compound wrapped in said amphiphilic polymer is fixated within said polymer.

12. The nano-sized particles as recited in claim 9, wherein said particles are substantially spherical.

13. The nano-sized particles as recited in claim 9, wherein said amphiphilic polymer is selected from the group consisting of: natural polysaccharides, polyacrylic acid, polyethylene imine, polymethacrylic acid, polyethylene oxide, polyvinyl alcohol, polyacetylene, polyisoprene and polybutadiene.

14. The nano-sized particles as recited in claim 9, wherein said active compound is a pharmaceutical compound.

15. The nano-sized particles as recited in claim 14, wherein said pharmaceutical compound is a chemotherapeutic agent or an antibiotic agent.

16. The nano-sized particles as recited in claim 9, wherein said particles are in the range of from approximately 10 to approximately 1000 nanometers in size.

17. The hydrophilic dispersion as recited in claim 1, wherein said nano-sized molecular entity is bioavailable in the human body.

18. The nano-sized particles as recited in claim 9, wherein said active compound is selected from the group consisting of: peptides, polypeptides, nucleotides and co-ferments, vitamins, steroids, porphyrins, metal-complexes, purines, pyrimidines, antibiotics, hormones and chemotherapeutic agents.

19. A hydrophilic inclusion complex consisting essentially of nano-sized particles of a water-soluble compound surrounded by and entrapped within an amphiphilic polymer, wherein said inclusion complex is water- soluble.

20. The hydrophilic inclusion complex as recited in claim 19, wherein said water-soluble compound interacts with said amphiphilic polymer via the formation of non-valent bonds.

21. The hydrophilic inclusion complex as recited in claim 20, wherein said non-valent bonds are electrostatic forces, Van der Waals forces or hydrogen bonds.

22. The hydrophilic inclusion complex as recited in claim 19, wherein said amphiphilic polymer does not form rigid matrices.

23. The hydrophilic inclusion complex as recited in claim 19, wherein said active compound entrapped within said amphiphilic polymer is fixated within said polymer.

24. The hydrophilic inclusion complex as recited in claim 19, wherein said active compound entrapped within said amphiphilic polymer is in the amorphous or partially crystalline state.

25. The hydrophilic inclusion complex as recited in claim 19, wherein said hydrophilic inclusion complex is bioavailable.

26. The hydrophilic inclusion complex as recited in claim 19, wherein said water-soluble active compound is a pharmaceutical compound.

27. A hydrophilic dispersion comprising a water-insoluble or water soluble active compound and an amphiphilic polymer which wraps said active compound to form a water-soluble nano-sized molecular entity in which non-valent bonds are formed between said active compound and said amphiphilic polymer such that said bonds fixate said active compound within said polymer, in which nano-sized molecular entity the active compound is in the amorphous or partially crystalline state and wherein said amphiphilic polymer does not form rigid matrices.

28. Nano-sized particles comprising a water-insoluble or water soluble active compound in an amorphous or partially crystalline state wrapped within an amphiphilic polymer such that non-valent bonds are formed between said active compound and said amphiphilic polymer, and said amphiphilic polymer does not form rigid matrices.

* * * * *